United States Patent [19]

Shuto et al.

[11] Patent Number: 5,051,499

[45] Date of Patent: * Sep. 24, 1991

[54] NOVEL NUCLEOSIDE-PHOSPHOLIPID CONJUGATE

[75] Inventors: Satoshi Shuto; Hiromichi Itoh; Kiyofumi Fukukawa; Masatoshi Tsujino, all of Shizuoka, Japan

[73] Assignee: Toyo Jozo Kabushiki Kaisha, Shizuoka, Japan

[*] Notice: The portion of the term of this patent subsequent to Jan. 10, 2006 has been disclaimed.

[21] Appl. No.: 445,965

[22] Filed: Nov. 28, 1989

Related U.S. Application Data

[62] Division of Ser. No. 102,043, Sep. 28, 1987, Pat. No. 4,921,951.

[30] Foreign Application Priority Data

Sep. 27, 1986 [JP] Japan .................................. 61-229203
Sep. 27, 1986 [JP] Japan .................................. 61-229204

[51] Int. Cl.$^5$ ..................... C07H 19/10; C07H 19/20; C07D 473/00
[52] U.S. Cl. ........................................ 536/29; 536/27; 536/28
[58] Field of Search .............................. 536/27, 29, 28

[56] References Cited

U.S. PATENT DOCUMENTS

| | | | |
|---|---|---|---|
| 4,291,024 | 9/1981 | Turcotte | 536/29 |
| 4,797,479 | 1/1989 | Shuto | 536/27 |
| 4,921,951 | 5/1990 | Shuto | 536/27 |

FOREIGN PATENT DOCUMENTS

| | | | |
|---|---|---|---|
| 1238793 | 10/1982 | Japan | 536/27 |
| 1152694 | 7/1986 | Japan | 514/51 |

OTHER PUBLICATIONS

"Phospholipid Derivatives of Necleoside Analogs as Prodrugs with Enhanced Catabolic Stability", Cancer Research, vol. 41, Jul. 1981, by T. Matsushita et al., pp. 2707-2713.

"Cytotoxic Liponucleotide Analogs", Biochimica et Biophysica Acta, 619, 1980, by J. G. Turcotte et al., pp. 619-631.

"Synthesis of Phospholiponucleosides", Synthesis, May 1982, by Fausto Ramirez et al., pp. 402-404.

Primary Examiner—Johnnie R. Brown
Assistant Examiner—James O. Wilson
Attorney, Agent, or Firm—Young & Thompson

[57] ABSTRACT

Novel nucleoside-phospholipid conjugates of the formula

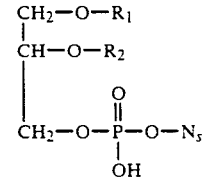

wherein $R_1$ is $C_{14-24}$ long chain aliphatic acyl or $C_{1-24}$ aliphatic alkyl, $R_2$ is $C_{2-10}$ aliphatic acyl or $C_{1-24}$ aliphatic alkyl and $N_s$ is a nucleoside residue; and pharmacologically acceptable salts thereof are prepared in a one-step reaction by reacting the corresponding nucleoside and glycerophospholipid derivative in the presence of phospholipase D-P.

2 Claims, No Drawings

NOVEL NUCLEOSIDE-PHOSPHOLIPID CONJUGATE

This application is a division of application Ser. No. 07/102,043, filed Sept. 28, 1987, now U.S. Pat. No. 4,921,451.

BACKGROUND OF THE INVENTION

1. Field of the Invention

The present invention relates to novel nucleoside-phospholipid conjugates and salts thereof. More particularly, the present invention relates to a nucleoside-phospholipid conjugate of the formula

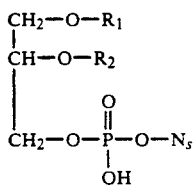

wherein $R_1$ is $C_{14-24}$ aliphatic acyl or $C_{1-24}$ aliphatic alkyl, $R_2$ is $C_{2-10}$ aliphatic acyl or $C_{1-24}$ aliphatic alkyl, and $N_s$ is a nucleoside residue, and salts thereof.

2. Description of the Prior Art

Nucleoside antitumor agents have been widely used as effective chemotherapeutics for neoplastic cells. In their application as antitumor-chemotherapeutics, however, several problems have arisen. For example, in the mechanism for the activity of nucleoside anti-neoplastic agents, in vivo phosphorylation of the hydroxyl group at the nucleoside 5' position is essential for antitumor activity; the agent is decomposed to an inactive substance by inactivation reactions such as phosphorolysis and deamination; the resistance of tumor cells to antitumor agents increases; and the agent is sometimes toxic to normal mitotic cells. Many kinds of nucleoside derivatives have been synthesized to overcome the disadvantages of known nucleoside antitumor agents.

CDP-diacylglycerol is known to have an important role as an intermediate in the biosynthesis of glycerophospholipid in vivo. Its analogue, arabinosylcytosine-phospholipid conjugate, which has antitumor activity, has been chemically synthesized [Biochim. Biophys. Acta, 619, 619–631 (1980), J. Med. Chem., 1982, 25, 1322–1329].

5-fluoro-2-deoxyuridine-phospholipid conjugate (Japan Unexam. Pat. Publ. No. 61-91195, No. 61-152694) and a process for manufacturing heterocyclic phospholipid conjugate by phospholipase DM (ibid. No. 61-88890) have also been reported.

This prior art has a number of disadvantages. Synthesis of these known compounds is a complicated multistep process with quite low overall yield. Moreover, these synthetic compounds are only sparingly soluble in aqueous media, and are thus difficult to use as injectable preparations.

Furthermore, previously reported nucleoside-phospholipid conjugates comprise an ester linkage of glyceride and a hydrophobic fatty acid in a phospholipid backbone, and hence are easily decomposed by phospholipase $A_1$ or phospholipase $A_2$ in vivo. Stability of these compounds is also unsatisfactory.

SUMMARY OF THE INVENTION

We have found that phospholipse D-P effectively catalyzes the transfer reaction of the phosphatidyl residue from glycerophospholipid to the primary hydroxyl group of a nucleoside. A heretofore unavailable variety of nucleoside-phospholipid conjugates can thus readily be prepare.

We have also found that nucleoside-phospholipid conjugates of the above formula, wherein $R_1$ is $C_{14-24}$ long-chain aliphatic acyl, $R_2$ is $C_{2-10}$ aliphatic acyl or aliphatic alkyl and $N_2$ is a nucleoside residue, and salts thereof, have superior solubility in aqueous media and have strong antitumor activity.

We have further found that ether type compounds such as nucleoside-dialkylether phospholipid conjugates or salts thereof are not decomposed by phospholipase $A_1$ or $A_2$ in vivo, and have strong antitumor activity.

An object of the present invention is to provide novel nucleoside-phospholipid conjugates of the formula

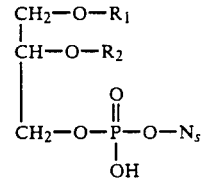

wherein $R_1$, $R_2$ and $N_s$ have the same meanings as before.

The term "alkyl" as used in the present specification means saturated alkyl or unsaturated alkyl such as alkenyl, alkadienyl or alkynyl.

Specifically, the group $R_1$ is $C_{14-24}$ long-chain aliphatic acyl or $C_{1-24}$ aliphatic alkyl. The $C_{14-24}$ long-chain aliphatic acyl may be saturated or unsaturated. Examples of straight chain saturated aliphatic acyl are myristoyl, palmitoyl, stearoyl, eicosanoyl, dosaconoyl and tetracosanoyl, and examples of unsaturated aliphatic acyl are palmito-oleoyl, oleoyl and 9,12-octadecadienoyl. The $C_{1-24}$ aliphatic alkyl may also be saturated or unsaturated, and it may be straight or branched. Examples of $C_{1-24}$ saturated aliphatic alkyl are methyl, ethyl, propyl, butyl, hexyl, heptyl, 3-heptyl, octyl, nonyl, decyl, 8-ethyldecyl, undecyl, lauryl, tridecyl, pentadecyl, hexadecyl (cetyl), heptadecyl, octadecyl (stearyl), nonadecyl nonadecynol and eicodecyl, and examples of $C_{2-24}$ unsaturated aliphatic alkyl are vinyl, allyl, 2-butenyl, 3-hexynyl, 4-decynyl, 6-tetradecenyl, 9-octadecenyl and linoleyl.

The group $R_2$ is $C_{2-10}$ aliphatic acyl or $C_{1-24}$ aliphatic alkyl. Examples of $C_{1-10}$ aliphatic acyl are acetyl, propynoyl, propanoyl, butanoyl, hexanoyl, octanoyl and decanoyl. Examples of $C_{1-24}$ aliphatic alkyl are the same as those for group $R_1$.

In the above compound, at least one of $R_1$ and $R_2$ is preferably $C_{14-24}$ aliphatic alkyl, for affinity with the cell membrane in vivo.

The group $N_s$ is a nucleoside residue, and is preferably a ribonucleoside residue such as 5-fluorouridine-5'-yl, bredinine-5'-yl, tubercidin-5'-yl and 5-fluorocytidine-5'-yl, an arabinosyl nucleoside residue such as arabinosyl cytosine-5'-yl, arabinosyl-5-fluorocytosine-5'-yl, arabinosyladenine-5'-yl and arabinosylthymine-5'-yl, a 2'-deoxyribonucleoside residue such as 5-fluoro- 2'-deoxyuridine-5'-yl, or a carbocyclic nucleoside residue such as neplanocin A-6'-yl.

Salts of the above compounds can be pharmacologically acceptable salts such as alkaline metal salts, alkaline earth metal salts, transition metal salts and organic base salts.

A nucleoside-phospholipid conjugate according to the present invention, and salts thereof, can be obtained by reacting a glycerophospholipid derivative of the formula

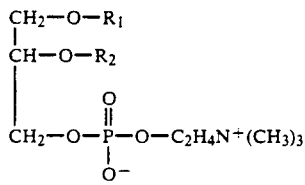

wherein $R_1$ and $R_2$ have the same meanings as before, with a nucleoside of the formula $N_s$—OH, for example a ribonucleoside such as 5-fluorouridine, bredinine, tubercidin or 5-fluorocytidine, or an arabinosyl nucleoside such as arabinosyl cytosine, arabinosyl-5-fluorocytosine, arabinosyladenine or arabinosyl thymine or a 2'-deoxyribonucleoside such as 5-fluoro-2'deoxyuridine, or a carbocyclic nucleoside such as neplanocin A, in the presence of phospholipase d-P in a suitable solvent.

A preferred example of phospholipase D-P in phospholipase D-P obtained by culturing a broth of Streptomyces sp. AA586 FERM P-6100 (Japan Pat. Unexam. Publ. No. 58-152481, Toyo Jozo Co., Catalog No. P-39). The amount of catalyst is at least 0.01 unit phospholipase D-P per 0.001 mole of phospholipid, and is preferably 1-100 units. Examples of a suitable solvent are two-phase systems of organic solvent and aqueous solvent, for example a mixture of organic solvent such as ether, benzene or chloroform and buffer solution of pH 3-9, preferably pH 4-6. A general example of a water soluble salt for generation of a metal ion is calcium chloride. Reaction temperature is generally 20°-60° C. and reaction time is 30 minutes to 30 hours, preferably 1-6 hours. The thus-obtained nucleoside-phospholipid conjugate according to the invention can be purified by a partition method and silica-gel chromatography.

One step synthesis of nucleoside-phospholipid conjugate of the present invention is illustrated as follows:

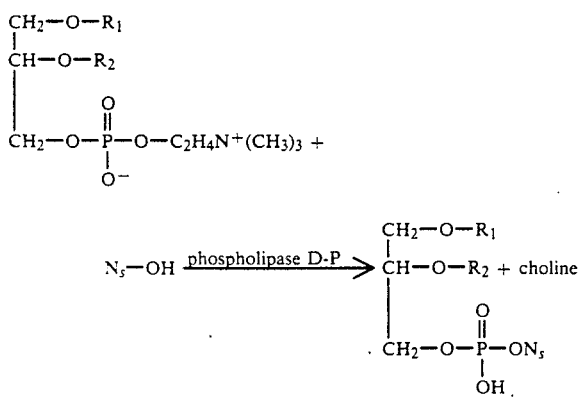

wherein $R_1$, $R_2$ and $N_s$ have the same meanings as before.

The thus-obtained product can be prepared as a non-toxic, pharmacologically acceptable salt, such as a sodium or potassium salt.

The thus-prepared nucleoside-phospholipid conjugate of the present invention has the advantages that: it is more lipophilic as compared with the original nucleoside; it is not easily excreted, that is, it is more active for a longer time; it is not affected by enzymatic inactivation reactions such as phosphorolysis, deamination and reduction; it has higher affinity for cell membranes; antineoplastic nucleoside 5'-monophosphate is generated in cells without action of kinase; and it has long action and increased activity with low toxicity.

The ester type nucleoside-phospholipid conjugate of the present invention is especially resistant to hydrolysis by phospholipase $A_1$ or phospholipase $A_2$ in vivo, and can be administered orally. Other types of nucleoside-phospholipid conjugates according to the present invention have the advantage of high solubility in water, and hence they can be prescribed not only in oral administration form but also as an injectable preparation.

The novel nucleoside-phospholipid conjugates of the present invention reveal marked antitumor activity in vivo, in addition to anti-metastatic activity on tumors, and anti-viral activity.

Antitumor activity against mouse leukemia P-388 carcinoma is shown in the ensuring examples, according to the following list of specifications:

Antitumor Activity

1. Samples: shown in Tables 1 and 2.
2. Animal: $BDF_1$ mice, age 5 weeks, male, Charles River Inc., 5 mice in an experimental group at 7 control mice.
3. Tumor cells: P-388 leukemic cells; $1 \times 10^6/0.2$ ml are inoculated intraperitoneally in $BDF_1$ mice of the experimental group.
4. Preparation of samples and administration of drugs:
   Samples are suspended in Tris-HCl saline solution by sonification. 0.1 ml/10g body weight is administered.
   Administration: starting one day after inoculation of tumor cells, once a day for 5 days intraperitoneally. Amount of dose is shown in the Tables.
5. Increase in life span (ILS) is calculated by the following equation:

$$ILS(\%) = \frac{\text{mean increased life span (days); experimental group}}{\text{mean survivals date (days); control group}} \times 100$$

Average survival date in control group is 7.86 days (7.57-7.93 days).

As shown in Table 1, each of the nucleoside-phospholipid conjugates illustrated in this table is administered at 3-10 mg/kg/day in $BDF_1$ mice of the experimental group, and each is shown to have strong antitumor activity, promoting an increased life span of 30-120%.

Also, as shown in Table 2, ester type nucleoside-phospholipid conjugates illustrated in this table is administered at 10-30 mg/kg/day in $BDF_1$ mice, and each is shown to have strong antitumor activity, promoting an increased life span of 30-150%.

TABLE 1

| nucleoside-phospholipid conjugate | | | dose | ILS |
|---|---|---|---|---|
| $R_1$ | $R_2$ | $N_5$ | (mg/kg) | (%) |
| palmitoyl | decanoyl | FUR | 3 × 5 | 61.2 |
| | | | 10 × 5 | 121.6 |
| " | octanoyl | FUR | 3 × 5 | 45.3 |
| | | | 10 × 5 | 79.7 |
| " | hexanoyl | FUR | 3 × 5 | 45.3 |
| | | | 10 × 5 | 79.7 |
| " | butanoyl | FUR | 3 × 5 | 36.1 |
| | | | 10 × 5 | 53.2 |
| palmitoyl | acetyl | FUR | 3 × 5 | 40.1 |
| | | | 10 × 5 | 58.9 |
| " | decanoyl | NEPA | 3 × 5 | 50.6 |
| | | | 10 × 5 | 89.4 |
| " | octanoyl | NEPA | 3 × 5 | 66.4 |
| | | | 10 × 5 | 84.9 |
| " | hexanoyl | NEPA | 3 × 5 | 34.7 |
| | | | 10 × 5 | 53.2 |
| " | butanoyl | NEPA | 3 × 5 | 48.0 |
| | | | 10 × 5 | 63.4 |
| " | acetyl | NEPA | 3 × 5 | 37.5 |
| | | | 10 × 5 | 55.1 |

FUR: 5-fluorouridine 5'-yl
NEPA: neplanocin A-6'-yl

TABLE 2

| Ester type nucleoside-phospholipid conjugate | | | dose | ILS |
|---|---|---|---|---|
| $R_1$ | $R_2$ | $N_5$ | (mg/kg) | (%) |
| cetyl | cetyl | FUR | 10 × 5 | 101.0 |
| | | | 30 × 5 | 127.0 |
| stearyl | stearyl | FUR | 30 × 5 | 31.0 |
| oleyl | oleyl | FUR | 10 × 5 | 74.0 |
| | | | 30 × 5 | 76.0 |
| cetyl | cetyl | NepA | 30 × 5 | 34.9 |
| stearyl | stearyl | NepA | 30 × 5 | 31.0 |
| oleyl | oleyl | NepA | 30 × 5 | 26.0 |
| cetyl | cetyl | AraFC | 10 × 5 | 68.0 |
| | | | 30 × 5 | 151.9 |
| stearyl | stearyl | AraFC | 30 × 5 | 61.0 |
| oleyl | oleeyl | AraFC | 10 × 5 | 81.0 |
| | | | 30 × 5 | 148.0 |

FUR: 5-fluorouridine-5'-yl
NePA: neplanocin A-6'-yl
AraFC: arabinosyl-5-fluorocytosine-5'-yl

Acute toxicity

The samples of Tables 1 and 2, suspended in Tris-HCl saline solution by sonification, are administered intraperitoneally at doses of 100 mg/kg for the compounds of Table 1 and 200 mg/kg for the compounds of Table 2. No signs of toxicity were observed.

The nucleoside-phospholipid conjugates of the present invention and salts thereof can be admixed with pharmacologically acceptable excipients in carrier or diluent form, and administered as tablets, capsules, granules, powders, injectable mixtures or suppositories, either orally or parenterally.

The daily dosage amount may be 1–500 mg for humans, with one or more doses per day; however, dosage will vary depending on the age, body weight, symptoms and condition of the patient.

The following examples illustrate the present invention but are not to be construed as limiting:

EXAMPLES 1–12

Nucleoside $N_s$—OH (amount shown in Table 3) was dissolved in 200 mM acetate buffer pH 6.0 (volume shown in Table 3) containing 250 mM $CaCl_2$, and the resultant solution was stirred at 45° C. for 3 mins. Phospholipase D-P (3mg, from Streptomyces, Toyo Jozo Co.) and a 0.3 mM chloroform solution (10 ml) of the phospholipid derivative indicated in Table 3 were added thereto, with the resultant mixture being stirred for 6 hours and then cooled. To the reaction mixture were added in 1N-HCl (5 ml), chloroform (30 ml) and methanol (25 ml), and the resultant mixture was then partitioned. The organic layer was washed twice with water and dried in vacuo. The residue was dried in vacuo after adding a small amount of ethanol, and was then dissolved in a small amount of chloroform, whereafter it was charged on a flash column of silica gel (2.5 × 10 cm) and eluted stepwise with chloroform, followed by a series of chloroform:methanol mixtures of relative concentrations (20:1), (15:1), (12:1), (10:1), (7:1), (5:1), (4:1) and (2:1) in this order. The eluate was dried in vacuo and the resultant residue was dissolved in a mixture of chloroform (40 ml) and methanol (20 ml), and separated by adding 0.5N-HCl (12 ml), then washed twice with water and dried to yield the product.

TABLE 3

| No | $R_1$ | $R_2$ | $N_s$—OH | Buffer solu. | Yield | PLDP | UVλmax | FAB mass spectrum | Rf |
|---|---|---|---|---|---|---|---|---|---|
| 1 | Palmitoyl | decanoyl | FUR, 10 eq. | B', 3 ml | 59% | 3 mg | 268 nm | 831 (M + Na) | 0.32 |
| 2 | " | " | NepA, 5 eq. | B', 5 ml | 63% | 3 mg | 260 nm | 832 (M + Na) | 0.28 |
| 3 | " | octanoyl | FUR, 10 eq. | B', 3 ml | 58% | 3 mg | 268 nm | 825 (M + 2 Na − H) | 0.31 |
| 4 | " | " | NepA, 5 eq. | B', 5 ml | 61% | 3 mg | 260 nm | 826 (M + 2 Na − H) | 0.25 |
| 5 | " | hexanoyl | FUR, 10 eq. | B', 3 ml | 69% | 3 mg | 268 nm | 797 (M + 2 Na − H) | 0.29 |
| 6 | " | " | NepA, 5 eq. | B', 5 ml | 73% | 3 mg | 260 nm | 776 (M + Na) | 0.23 |
| 7 | " | butanoyl | FUR, 10 eq. | B', 3 ml | 68% | 3 mg | 268 nm | 769 (M + 2 Na − H) | 0.26 |
| 8 | " | " | NepA, 5 eq. | B', 5 ml | 72% | 3 mg | 260 nm | 748 (M + Na) | 0.22 |
| 9 | " | acetyl | FUR, 10 eq. | B', 3 ml | 65% | 3 mg | 268 nm | 741 (M + 2 Na − H) | 0.21 |
| 10 | " | " | NepA, 5 eq. | B', 5 ml | 69% | 3 mg | 260 nm | 742 (M + 2 Na − H) | 0.17 |
| 11 | stearoyl | octyl | NepA, 5 eq. | B', 5 ml | 62% | 3 mg | 260 nm | 818 (M + Na) | 0.27 |
| 12 | " | " | FUR, 20 eq. | B', 5 ml | 55% | 3 mg | 268 nm | 719 (M + Na) | 0.22 |

B': 200 mM acetate buffer (pH 6.0) containing 250 mM $CaCl_2$
PLDP: Phospholipase D-P (specific activity: 160 units/mg)
UV: measured in chloroform-methanol (1:2)
Rf: developer: chloroform: methanol: water (65:25:30) Plate; Merck, Art 5715 Spot was detected by UV and molybden-blue reagent.

EXAMPLES 13–22

Nucleoside $N_s$—OH (amount shown in Table 4) was dissolved or suspended in 200 mM acetate buffer pH 6.0 (volume shown in Table 4) containing 250 mM $CaCl_2$ and the resultant mixture was stirred at 45° C. for 3 minutes. Phospholipase D-P (amount shown in Table 4) and 20 ml of a 0.3 mM chloroform solution of phospholipid derivative (shown in Table 4) were added thereto and the resultant mixture was stirred for 6 hours and then cooled. 1N-HCl (5 ml), chloroform (30 ml) and methanol (25 ml) were added thereto and the organic layer was separated. The organic layer was washed twice with water and dried in vacuo. A small amount of ethanol was added to the residue and the resulting solution was dried in vacuo. The residue was dissolved in a small amount of chloroform and charged on a flash column of silica gel (2.5×10 cm), where it was eluted stepwise with chloroform followed by a series of mixtures of chloroform:methanol (20:1), (15:1), (12:1), (10:1), (7:1), (5:1), (4:1) and (3:1), in this order. The eluate was dried in vacuo and the residue was dissolved in a mixture of chloroform (40 ml) and methanol (20 ml). 0.5N-HCl (12 ml) was then added to separate the organic layer, which was washed twice with water. The residue was dried in vacuo to obtain the desired product.

NMR (CDCl$_3$:CD$_3$OD=2:1):

1: ppm 7.85 (d, 1H, J$_{6F}$=6.3H), 5.89 (bs, 1H), 4.3–3.9 (m, 7H), 3.53 (m, 7H), 1.55 (br, 4H), 1.26 (s, 52H), 0.88 (t, 6H).

2: ppm 8.23 (s, 1H), 8.19 (s, 1H), 5.89 (bs, 1H), 5.52 (m, 1H), 4.72 (m, 3H), 4.28 (m, 1H), 4.02 (m, 2H), 3.59 (m, 7H), 1.55 (br, 4H), 1.27 (s, 52H), 0.88 (t, 6H).

3: ppm 8.22 (d, 1H, J$_{6F}$=6.5H), 6.11 (bs, 1H), 4.3–4.0 (m, 7H), 3.53 (m, 7H), 1.55 (br, 4H), 1.26 (s, 52H), 0.88 (t, 6H).

TABLE 4

| No | R$_1$ | R$_2$ | N$_s$—OH | Buffer solu. | Yield | PLDP | UVλmax | FAB mass spectrum | Rf |
|---|---|---|---|---|---|---|---|---|---|
| 1 | cetyl | cetyl | FUR, 20 eq. | 3 ml | 60% | 3 mg | 268 nm | 887 (M + NBa) | 0.33 |
| 2 | " | " | NePA, 5 eq. | 7 m | 73% | 3 mg | 260 nm | 866 (MH) | 0.30 |
| 3 | " | " | AraFC, 10 eq. | 3 ml | 36% | 3 mg | 283 nm | 886 (M + Na) | 0.24 |
| 4 | 9-octadecenyl | 9-octadecenyl | FUR, 20 eq. | 5 ml | 62% | 2 mg | 268 nm | 939 (M + Na) | 0.39 |
| 5 | 9-octadecenyl | 9-octadecenyl | NepA, 5 eq. | 7 ml | 78% | 2 mg | 260 nm | 940 (M + Na) | 0.34 |
| 6 | stearyl | octyl | NepA, 5 eq. | 7 ml | 59% | 5 mg | 260 nm | 804 (M + Na) | 0.25 |
| 7 | stearyl | methyl | FUR, 20 eq. | 5 ml | 51% | 5 mg | 268 nm | 705 (M + Na) | 0.21 |
| 8 | cetyl | methyl | FUR, 20 eq. | 5 ml | 55% | 5 mg | 268 nm | 677 (M + Na) | 0.20 |
| 9 | cetyl | hexyl | FUR, 20 eq. | 5 ml | 61% | 5 mg | 268 nm | 747 (M + Na) | 0.25 |

Abbreviations are the same as in Table 3

What is claimed is:

1. A compound of the formula

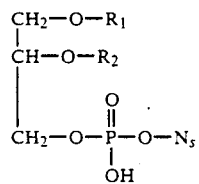

wherein R$_1$ is C$_{14-24}$ long chain aliphatic acyl, R$_2$ is C$_{2-10}$ aliphatic acyl and N$_s$ is 5-fluorouridine-5'-yl; and pharmacologically acceptable salts thereof.

2. Compound according to claim 1 wherein R$_1$ is C$_{16-18}$ long chain aliphatic acyl.

* * * * *